United States Patent

Moreau DeFarges et al.

[11] Patent Number: 5,879,327
[45] Date of Patent: Mar. 9, 1999

[54] NEEDLELESS JET INJECTION DEVICE

[76] Inventors: Alain Moreau DeFarges, 2 Avenue Leopold II, Paris, France, F-75016; Xavier Moreau DeFarges, 2 Boulevard Du Roi, Versailles, France, F78000

[21] Appl. No.: 722,002
[22] PCT Filed: Apr. 6, 1995
[86] PCT No.: PCT/FR95/00445
    § 371 Date: Oct. 1, 1996
    § 102(e) Date: Oct. 1, 1996
[87] PCT Pub. No.: WO95/27523
    PCT Pub. Date: Oct. 19, 1995

[30] Foreign Application Priority Data

Apr. 6, 1994 [FR] France ................... 94 04041
Oct. 24, 1994 [FR] France ................... 94 12692

[51] Int. Cl.$^6$ .................................................. A61M 5/30
[52] U.S. Cl. ........................................ 604/68; 604/135
[58] Field of Search ................... 604/68, 135, 49

[56] References Cited

U.S. PATENT DOCUMENTS 5,334,144  8/1994  Alchas et al. ................... 604/135 X
5,599,302  2/1997  Lilley et al. ................... 604/135 X Primary Examiner—Wynn Wood Coggins
Assistant Examiner—N. Kent Gring
Attorney, Agent, or Firm—Omri M. Behr, Esq.

[57] ABSTRACT

Needleless jet-injection device, characterized in that it consists of a body (1) having at one of its ends (4, 5) a cap (3), which, thanks to a relative movement between these elements, may drive a loading mechanism (2), co-operating with an impact component (17) which has to strike the piston of a cartridge (28) which is made of a material that does not pollute the environment and which contains the active product to be injected, this cartridge (28) being moreover placed at the other end of the said magazine-less body (1) and in the axis of said impact component (17), for single use.

21 Claims, 3 Drawing Sheets

NEEDLELESS JET INJECTION DEVICE

The present invention relates to a device which allows a product, particularly a pharmaceutical product, to be injected into the bodies of humans or animals.

In particular, it refers to an apparatus which does not have a hypodermic needle, and is provided with a loading system that allows the cutaneous or muscular administration of medicinal or vaccinal substances, contained in a single use, cartridge forming dose.

Needleless, transcutaneous, jet-injection apparatuses which have been developed for veterinary or human medicine are already known. The absence of a needle simplifies usage of the apparatus and does not require specific knowledge on the part of the user. They are generally employed for mass vaccination campaigns and are designed so that they may be quickly operated by non-specialist staff. By resorting to a jet, there is maximum avoidance of bacterial and/or viral contamination from one subject to another, which occurred in cases where the same needle was used on several subjects without sterilization. These apparatuses are generally made in the form of a gun, equipped with a container for the product to be injected, operated through a nozzle, through the action of a piston moving in a chamber which was beforehand filled with the substance, the piston being actuated by a hammer, or comprising a breech or magazine enclosing a cartridge placed evenly in the axis of the hammer.

Having taken into consideration the mode of action of the hammer, which has an important kinetic energy before it reaches the piston of the cartridge, which in the case where the cartridge is incorrectly positioned in the magazine of the gun, may induce explosion thereof at the start of the injection, these apparatuses are not reliable and are not easy to put into operation for utilisation not involving frequent use.

The present inventon is thus concerned with the elimination of these drawbacks, by proposing a device, which does not have a magazine for the cartridge, which allows the needleless jet-injection of the product contained in a cartridge placed directly in the head of said device, under stringent aseptic conditions, for single unit use.

To this end, the needleless jet-injection device is characterised in that it consists of a body having at one of its ends a cap, which, thanks to a relative movement between these elements, may entrain a loading mechanism, co-operating with an impact component which has to strike the piston of a cartridge containing the active product to be injected, this cartridge being positioned moreover at the other end of the said magazine-less body and in the axis of said impact component.

According to another advantageous characteristic of the invention, the needleless jet-injection device is characterised in that between the cap and the loading mechanism, there is a disengagable connection means.

Other characteristics and advantages of the present invention will become evident from the following description, with reference to the attached drawings, which illustrate an example of realisation which is in no way limited. In the figures.

Figure 1:
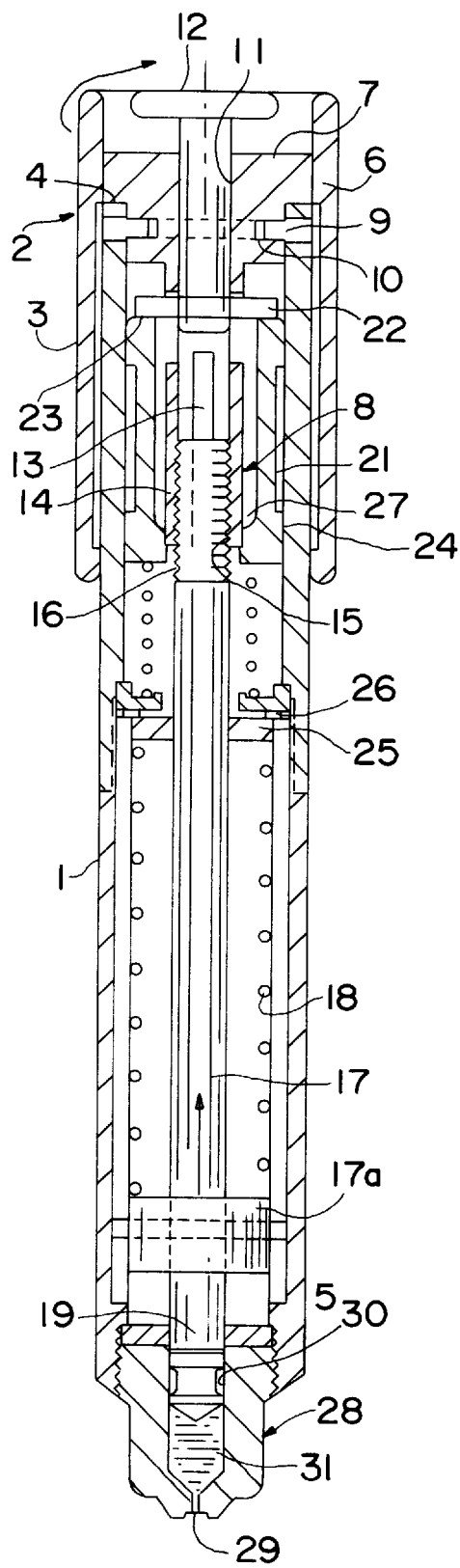
FIG. 1 is a plan view, in frontal elevation and in section, of the device according to the invention, in loaded position.
Figure 2:
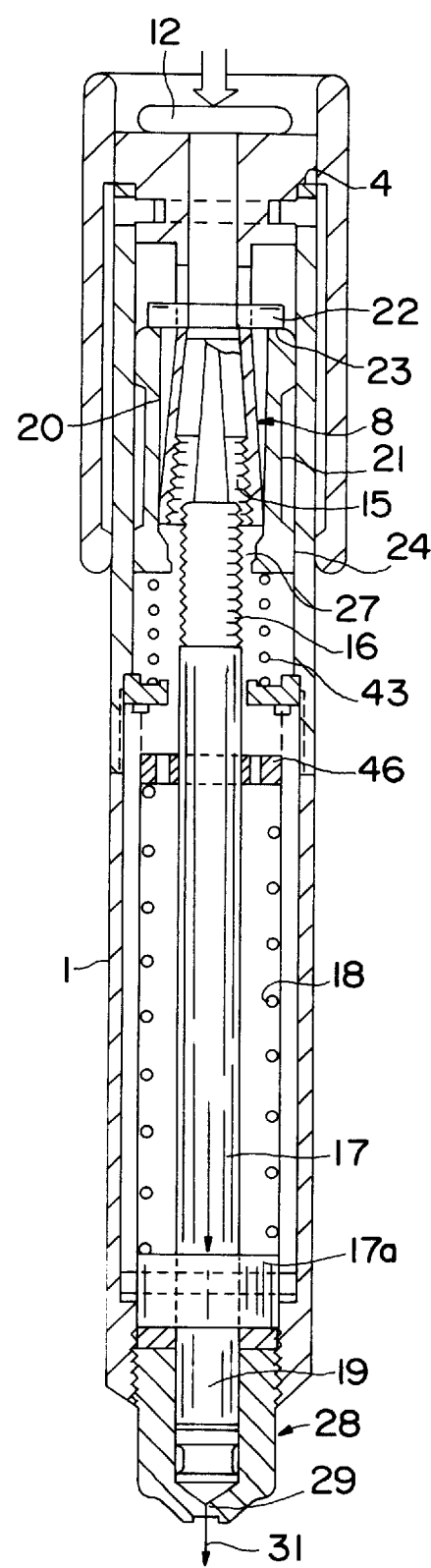
FIG. 2 is a plan view, in frontal elevation and in section, of the device according to the invention, in triggered position.
Figure 3:
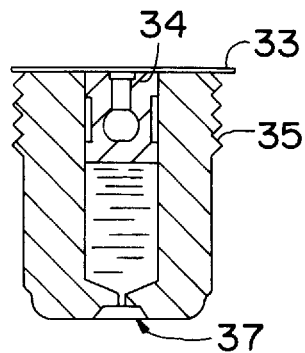
FIG. 3 is a large-scale view in section of a cartridge containing one dose of the injectable product.
Figure 4:
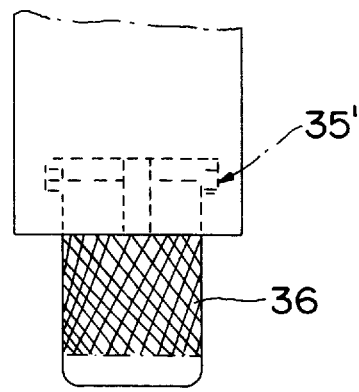
FIG. 4 is a view illustrating another method of fixing the cartridge onto the device.
Figure 5:
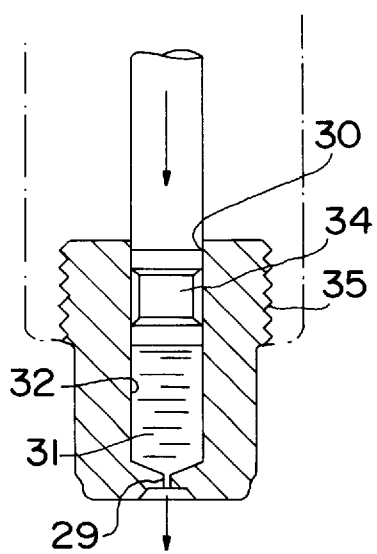
FIG. 5 is a view in section illustrating the movement of the hammer on the elastomeric button contained in the cartridge.
Figure 6:
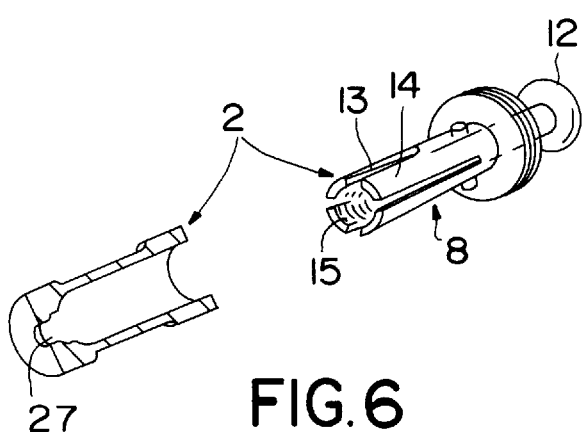
FIG. 6 is a view in perspective of the clamping system which compels the rod of the hammer to be grasped.
Figure 7:
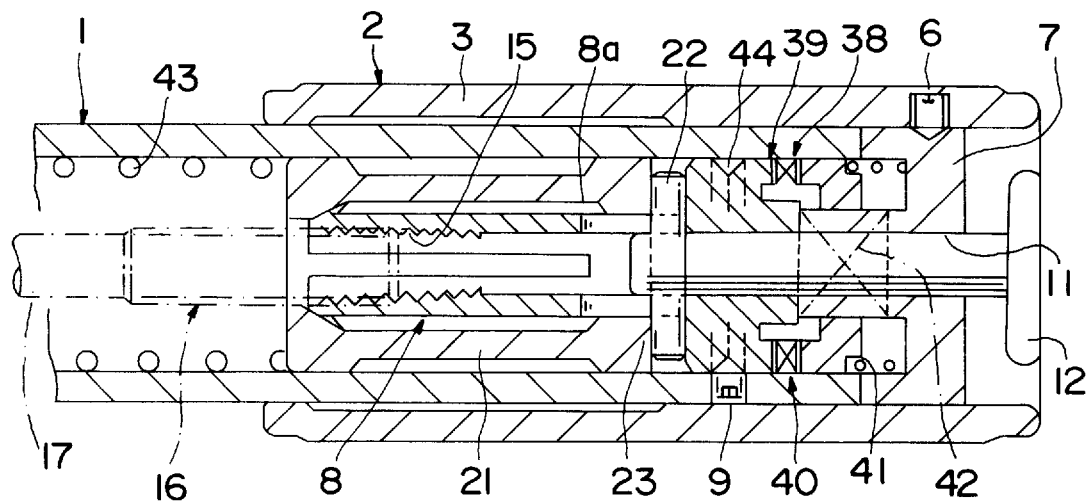
FIG. 7 is a plan view, in frontal elevation and in section, of the device according to another mode of the invention, consisting of a disengagable connection means.
Figure 8:
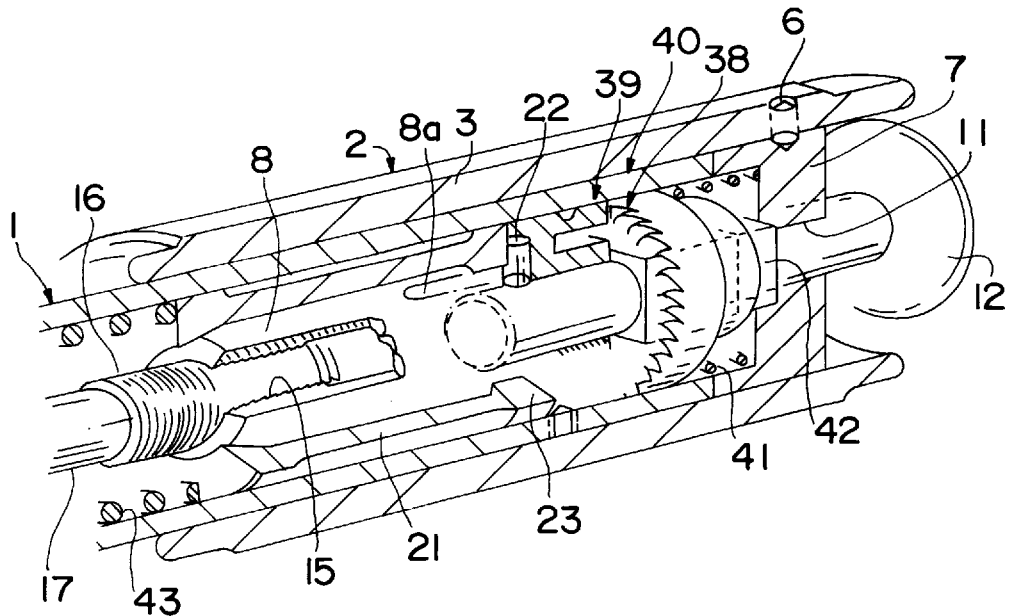
FIG. 8 is a view in perspective of the disengagable connection means.

According to a preferred embodiment, the device which is the object of the invention consists essentially of a body 1 extending in the shape of a tube, particularly of cylindrical cross-section, which is designed to accept a loading mechanism 2 connected to a cap 3 having in particular a milled edge so as to improve the grip for the user, which is provided at one of the ends 4, 5 of said body. The cap is made from a portion of tube, of similar section to that of the main body of said device, the diameter of which however is greater, so as to allow relative rotational movement around the body, and it co-operates through the intermediary of a coupling device 6, notably of the needle-screw type with a collar 7, the latter being bound up with a clamp 8. Said collar is fitted with play to the end of the body 1 and is able to turn freely in the latter, its axial position in the tube being determined by means of a radial stop 9 on the wall of the tube, and emerging into a circular channel 10 made on said collar 7, which is positioned facing the stop 9. The rotational movement from the cap 3 is conveyed through the intermediary of the coupling device 6 on the collar.

The said collar 7 is further provided with a central cavity 11 for passage of a hammer 12, which has free axial translatory, movement, and emerges inside the said clamp 8. This clamp constitutes one of the links of the loading device. Of essentially cylindrical shape, it is provided with a plurality of slots 13 which are essentially parallel to the axis of the body, so as to conform the shape of a plurality of flexible clips 14. The internal bore 15 of said clamp 8 is also provided with impressions enabling it to be screwed onto a threaded portion 16 provided on a rod 17 forming the hammer. The pitch of the thread is determined as a function of the chosen reduction and the tension constant of a spring 18. The impact of the hammer may similarly be adjusted by pre-setting the collapse of the spring, the inter-spiral space being controllable through the intermediary of a knurling wheel 46 moving along the rod 17 and in contact with 18 or through the intermediary of a stack of washers placed between the spring 18 and a collar 25. The coils of the spring 18 are compressed by the relative rotational movement between the cap 3 and the body 1.

Thus, a rod 17, forming a piston, is placed inside said body 1, its length being selected such that its end 19, not attached to said clamp 8, lies flush with one of the front surfaces 4, 5 of the body 1, when the loading mechanism 2 is operational.

The peripheral jacket 20 of the clamp is enclosed by a cross-piece 21, also of similar section to that of the body, the external diameter of which corresponds to the internal diameter of the body, so as to form guide zones. Its axial position inside the body is limited on one hand, at one of its ends 23, 24, by a pin 22 crossing radially right through the hammer 12, and on the other hand its other front end forms a support surface for a spring 43; the axial position of the spring and its other support surface are further limited for example by a collar 25 inserted in the body integrally with said rod 17 and immobilised axially if required by a circlip 26 or by a shoulder made on the rod.

In the loaded position, the user imparts a relative rotational movement between the body 1 and the cap 3; as we have seen before, the rotational movement of the cap is transferred both to said collar 7 and to the clamp 8 which is integral with the latter; the few threads of said clamp 8 engaged with those of the rod allow translatory movement to start between the rod 17 (forming the screw) and the clamp 8 (forming a nut) and allow these two pieces to approach one another. This translatory movement compresses the coils of the spring 18 until the inter-spiral space is reduced as far as possible. According to another embodiment, the spiral spring may be replaced by a helical spring or by any other elastic device.

In the disarmed or releasing position, the user imparts a slight push on the hammer 12, the joining pin 22 being radially salient, and upon contact with one of the frontal faces 23, 24 of the cross-piece, transmits a relative translatory movement between the cross-piece 21 and the clamp 8, which disengages the end thereof from a conical face 27 provided at the bottom of the bore of said cross-piece 21. The thrust of the spring 18, combined with the flexibility of the clips of the clamp, frees the respective threads previously engaged, thus inducing a almost impulsive translatory movement to the whole rod.

According to another embodiment of the invention, a connection means 38 is positioned between the cap 3 and the integral loading component of the clamp 8 contained in the body 1, and this connection means only allows relative rotational movement between these two pieces in one direction of rotation. In order to avoid any deterioration of the apparatus, and to simplify handling thereof by the user, a connecting means 38 is indeed disengageable and principally comprises two pieces 39, 40 particularly of circular section. One of the pieces 39 is integral with the cap 3, while the other 40 is connected to the clamp 8 and to the body 1 through the intermediary of a groove 44, in addition, each of the pieces has at its contact surface a plurality of embossed areas 41. These areas 41 are of a profile which is suitable to allow on one hand a relative sliding movement between the pieces 39 and 40 in one direction of rotation between the cap 3 and the body 1 and on the other hand to transmit the torque in the other direction of rotation of the cover 3 in relation to the body 1.

It is preferable for the embossed areas 41 to be made from a plurality of teeth, particularly with a triangular cross-section.

In order that the connection means 38 may function, it is however advisable not to totally suppress the movements of pieces 39 and 40 in relation to the cap 3 and to the clamp 8; in this way, when the connecting means is active (disengaged), the pieces 39, 40 have to break free longitudinally in relation to one another, and these pieces have to return to their engaged position after suppression of the torque; thus, an elastic component 41, particularly a spring type, is positioned upright to the exterior surface of one of the pieces 39 or 40, at the position of a guiding part 42, which compensates the translatory movement between the pieces.

According to another characteristic of the invention, at the other end 5 of the body 1 of said device, a cartridge 28 is placed by known means, in particular by screw means, by clipping (bushing, bayonette).

The cartridge 28, made from plastics or metallic material, or of glass, and overall of essentially cylindrical shape, includes an aperture 29, 30 at each end. One 30 of the apertures has a diameter essentially equivalent to the diameter of the rod 17, while the other 29, of small diameter, especially in the order of a few tenths of a millimeter, serves as a nozzle. The internal cavity of said cartridge is filled under vacuum with an active substance 31 and is optionally covered by a film 32 of a material which is compatible with the physical-chemical properties of said product, so as to limit as far as possible the incidence of adsorption. The cartridge 28 thus obtained is for single usage and is thus discardable.

In another respect, it is allowed for interposing an elastomeric piston 34 between the dose of product contained in the cavity of the cartridge and the surrounding area, in order to seal in the dose, this piston having to convey to the liquid the pressure exerted by the rod 17 which forms a hammer at its end 19. At the level of the cartridge aperture 30, this elastomeric piston is covered by a lid 33, in order to guarantee satisfactory aseptic conditions. This lid is removed at the time of installation of the cartridge 28 on the device.

According to another mode of use of the cartridge 28, the latter is empty and is filled by the user just before usage.

The peripheral jacket of said cartridge has on one hand fixing means 35, 35' to said body (thread pitch, wedges . . . ), and on the other hand embossed areas 36 for its gripping by the user. The front face corresponding to the nozzle optionally contains a cuvette 37, the depth of which is variable but guarantees that the jet coming from the aperture of the nozzle has enough time to be hydrodynamically established before the single subcutaneous, intradermal or intramuscular injection.

The invention as described above is very simple to use: there is no more sterilization, nor washing of the apparatus, whilst guaranteeing increased safety for the user due to the absence of a needle and the impossibility of effecting re-use without prior reloading with a new dose in the apparatus, the fixing mode of the cartridge avoiding any risk of bursting of the latter due to the absence of a breech. This invention is advantageously adapted to usage by an individual user having no specific knowledge of the matter relating to subcutaneous, intradermal or intramuscular injections, on one hand it suppresses the risk of accidents, which are always possible with injection means using a needle, and on the other hand it reduces the fear of injections as well as any risk of contamination. Furthermore, the use of this device allows the chronobiology of the patient to be respected. This invention finds advantageous developments in the injection of a dose of low volume, which may reach in particular 0.05 to 0.2 ml. It is of particular interest for the administration of medicines or vaccines to humans or animals. Among other products, polypeptides or peptides may be mentioned, such as enzymes and especially calcitonin, used for the prevention of bone loss and for the treatment of osteoporosis, or also anti-migraine medicaments. Other products, in particular polypeptides or peptides, which may be administered by the device according to the invention, include hormones, such as insulin, somatostatin, growth hormone, coagulation factors, for example anti-haemophilia factors, plasma constituents, such as erythropoyetin, anti-viral polypeptides, such as interferons or immuno-modulators, such as lymphokines. This device is similarly especially appropriate for the administration of vaccinal preparations.

It should be understood that the present invention is not limited to the embodiments described and represented above, but that it embraces all the variants. In this way, the cartridges may be located in front of the rod of the hammer with the assistance of a barrel or magazine, and these may similarly contain the dose of the product to be injected.

It is claimed:

1. A reusable needleless jet injection device for the injection of an active product, comprising:
   a tubular member;
   an axially displaceable impacting member;
   a cap mounted at one of the ends of said tubular member;
   a loading device coupled to said cap for being entrained, in response to relative movement between said tubular member and said cap, said loading device cooperating with said axially displaceable impacting member; and
   a disposable cartridge which is adapted to assume a first position, in which it is not secured to said apparatus, and a second position in which it is secured to the end of said tubular member opposite said cap in the axis of said impacting member, said cartridge comprising
   (a) attaching means adapted to cooperate with the tubular member to secure the cartridge in the second position,
   (b) an internal cavity adapted to contain the active product to be injected;
   (c) a first aperture acting as a nozzle at its end which is to be furthest away from the tubular body in said second position;
   (d) a second aperture at its end which is to be closest to the tubular member in the second position, and
   (e) a piston closing the cavity on the side of the second aperture, wherein in said first position, the cartridge contains the active product, the piston being in that case interposed between the active product and the surroundings and closing the cavity on the side of the second aperture, while in said second position the piston is adapted to be struck by the impacting member and to communicate to the active product a pressure exerted by the impacting member.

2. A device according to claim 1, wherein the cap cooperates via an attaching device with a ring placed at the top of the tubular member, said ring being connected to a clamp having a plurality of slots oriented substantially parallel with the axis of the tubular member, to produce a plurality of flexible tabs, said clamp having an internal bore so tapped as to produce impressions adapted to cooperate around a threaded portion with which a rod forming the impacting member is formed.

3. A device according to claim 2, wherein the ring has a central cutaway through which a striking pin making a free axial traversing movement passes which extends into the interior of said clamp, and the peripheral envelope of the clamp is clamped by a strut whose external diameter corresponds to the internal diameter of the tubular member, to produce guiding zones, the axial position of the strut inside the tubular member being limited at one of its ends by a pin which extends radially through the striking pin and is adapted to transmit to the strut the axial traversing movement of the striking pin, the other end face of said strut forming a bearing surface for a spring which biases the strut to its inoperative position.

4. A device according to claim 3, wherein the intensity of the striking pin is adjusted by the pre-adjustment of the compression of a trigger spring by means of a roller moving on the rod.

5. As A device according to claim 3, wherein the intensity of the striking pin is adjusted by the pre-adjustment of the compression of a trigger spring by means of a stack of washers disposed between the trigger spring and the ring.

6. A needleless injection device according to claim 1, wherein a disengagement linking member is interposed between the cap and the loading device.

7. A device according to claim 6, wherein the linking member allows the relative rotational movement between the cap and the tubular member in only one direction of rotation.

8. A device according to claim 7, wherein the linking member comprises two members of circular section whose contacting face is formed with a plurality of zones in raised relief, said zones having a profile which is adapted on the one hand to allow a relative sliding between the members move in one direction of rotation between the cap and the tubular member and on the other hand to transmit the torque in the other direction of rotation of the cap in relation to the tubular member.

9. A device according to claim 6, wherein the linking member comprises two members of circular section whose contacting face is formed with a plurality of zones in raised relief, said zones having a profile which is adapted on the one hand to allow a relative sliding between the members and in one direction of rotation between the cap and the tubular member and on the other hand to transmit the torque in the other direction of rotation of the cap in relation to the tubular member.

10. A disposable needleless cartridge for the jet injection of an active product, which is adapted to be secured to one end of the tubular member of a breechless injection device, and which comprises: at its other end a cap which, as the result of a relative movement between the tubular member and the cap, can entrain a loading device cooperating with an axially displaceable impacting member, said cartridge comprising securing means adapted to cooperate with the tubular member to releasably secure the cartridge thereto in the axis of the impacting member; an internal cavity adapted to contain the active product to be injected; a first opening acting as a nozzle at its end which is to be furthest away from the tubular member when the cartridge is secured thereto; a second opening at its end which is to be closest to the tubular member; and a piston closing the cavity on the side of the second opening, wherein before being secured to the tubular member, the cartridge contains the active product, the piston then being interposed between the active product and the surroundings and closing the cavity of the side of the second opening, and the piston is adapted to be struck by the impacting member and to communicate to the active product the pressure exerted by the impacting member when the cartridge is secured to the tubular member.

11. A cartridge according to claim 10, wherein the piston is covered by a diaphragm adapted to be removed before the cartridge is installed on the tubular member.

12. A cartridge according to claim 11, characterised in that the cartridge is made of plastics, metal, glass.

13. A cartridge according to claim 10, characterised in that the cartridge is made of plastics, metal, glass.

14. A cartridge according to claim 10, wherein the cavity is coated with a film of material suitable for the maximum limitation of absorption.

15. A cartridge according to claim 10, wherein the cartridge is filled in vacuo with said active product.

16. A cartridge according to claim 10, wherein the external envelope of said cartridge has zones in raised relief to be grasped by the user.

17. A cartridge according to claim 10, wherein the end face corresponding to the nozzle comprises a cuvette of variable depth, to ensure that the jet emerging from the nozzle opening has enough time to become hydrodynamically established before the subcutaneous, introdermal, intramuscular injection.

18. A cartridge according to claim 10, wherein the cartridge contains a single dose of a medicament which is intended to be administered by subcutaneous, intramuscular, intradermal injection.

19. A cartridge according to claim 10, wherein the cartridge contains polypeptides or peptides, such as enzymes, hormones, coagulation factors, antiviral products.

20. A cartridge according to claim 10, wherein the cartridge contains calcitonin.

21. A cartridge according to claim 10, wherein the cartridge contains a vaccine.

* * * * *